US00PP13838P29

(12) United States Plant Patent
Fruehwirth

(10) Patent No.: US PP13,838 P2
(45) Date of Patent: May 20, 2003

(54) POINSETTIA PLANT NAMED 'ECKAKEEM'

(75) Inventor: Franz Fruehwirth, Encinitas, CA (US)

(73) Assignee: Paul Ecke Ranch, Encinitas, CA (US)

( * ) Notice: Subject to any disclaimer, the term of this patent is extended or adjusted under 35 U.S.C. 154(b) by 0 days.

(21) Appl. No.: 10/087,971

(22) Filed: Mar. 4, 2002

(51) Int. Cl.[7] ..... A01H 5/00

(52) U.S. Cl. ..... Plt./307

(58) Field of Search ..... Plt./307, 303

(56) References Cited

PUBLICATIONS

UPOV–ROM GTITM Computer Database Mar. 2002, GTI Jouve Retrieval Software, Citation for Euphorbia 'Eckakeem'.*

* cited by examiner

*Primary Examiner*—Bruce R. Campell
*Assistant Examiner*—June Hwu
(74) *Attorney, Agent, or Firm*—C. A. Whealy

(57) ABSTRACT

A new and distinct cultivar of Poinsettia plant named 'Eckakeem', characterized by its inflorescences with dark red-colored flower bracts; dark green-colored leaves; uniform and mounded plant habit; early flowering habit; and excellent post-production longevity.

1 Drawing Sheet

BOTANICAL CLASSIFICATION/CULTIVAR DESIGNATION

*Euphorbia pulcherrima* Willd. cultivar Eckakeem.

BACKGROUND OF THE INVENTION

The present Invention relates to a new and distinct cultivar of Poinsettia plant, botanically known as *Euphorbia pulcherrima* Willd., and hereinafter referred to by the name 'Eckakeem'.

The new Poinsettia is a product of a planned breeding program conducted by the Inventor in Encinitas, Calif. The objective of the breeding program is to create new Poinsettia cultivars having flower bracts with desirable colors, uniform plant habit and excellent post-production longevity.

The new Poinsettia originated from a cross made by the Inventor of the *Euphorbia pulcherrima* Willd. cultivar Gutbier Marlene, disclosed in U.S. Plant Pat. No. 8,735, as the female, or seed, parent, with the *Euphorbia pulcherrima* Willd. cultivar 792, not patented, as the male, or pollen, parent. The cultivar Eckakeem was discovered and selected by the Inventor as a flowering plant within the progeny of the stated cross in a controlled environment in Encinitas, Calif., in December, 1998. The selection of this plant was based on its dark red-colored flower bracts.

Asexual reproduction of the new Poinsettia by terminal cuttings propagated in a controlled environment in Encinitas, Calif., since April, 1999, has shown that the unique features of this new Poinsettia are stable and reproduced true to type in successive generations of asexual reproduction.

BRIEF SUMMARY OF THE INVENTION

The following traits have been repeatedly observed and are determined to be the unique characteristics of 'Eckakeem'. These characteristics in combination distinguish 'Eckakeem' as a new and distinct cultivar:

1. Inflorescences with dark red-colored flower bracts.
2. Dark green-colored leaves.

3. Uniform and mounded plant habit.
4. Early flowering; natural season flower maturity date is early December for plants grown in Encinitas, Calif.; response time, about 9 weeks.
5. Excellent post-production longevity.

Plants of the new Poinsettia differ primarily from plants of the female parent, the cultivar Gutbier Marlene, in flower bract coloration as plants of the cultivar Gutbier Marlene have bright red-colored flower bracts. In addition, plants of the new Poinsettia have darker green-colored leaves and are more vigorous than plants of the cultivar Gutbier Marlene.

Plants of the new Poinsettia differ primarily from plants of the male parent, the cultivar 792, primarily in flower bract coloration as plants of the cultivar 792 have darker red-colored flower bracts. In addition, plants of the new Poinsettia are not as vigorous as plants of the cultivar 792.

Plants of the new Poinsettia can be compared to plants of the cultivar 490, disclosed in U.S. Plant Pat. No. 7,825. In side-by-side comparisons conducted in Encinitas, Calif., plants of the new Poinsettia had lighter red-colored bracts and flowered about 8 to 12 days later than plants of the cultivar 490.

BRIEF DESCRIPTION OF THE PHOTOGRAPHS

The accompanying colored photographs illustrate the overall appearance of the new Poinsettia, showing the colors as true as it is reasonably possible to obtain in colored reproductions of this type. Colors in the photographs may differ slightly from the color values cited in the detailed botanical description which accurately describe the colors of the new Poinsettia.

The photograph at the top of the sheet comprises a side perspective view of a typical flowering plant of 'Eckakeem' grown in a 16.5-cm container.

The photograph at bottom of the sheet comprises a top perspective view of a typical flowering plant of 'Eckakeem'.

DETAILED BOTANICAL DESCRIPTION

The new Poinsettia has not been observed under all possible environmental conditions. The phenotype may vary somewhat with variations in environment such as temperature, daylength and light intensity, without, however, any variance in genotype.

The aforementioned photographs, following observations and averaged measurements describe plants grown in Encinitas, Calif. during the autumn and winter under commercial practice in a polycarbonate-covered greenhouse with day temperatures about 24 to 29° C., night temperatures about 19° C., and light levels about 4,000 foot-candles. Single plants were grown in 16.5-cm pots and pinched once. Plants were flowered under natural season short day/long night conditions. Plants were about 18 weeks from unrooted cuttings when the photographs and the detailed botanical description were taken.

In the following description, color references are made to The Royal Horticultural Society Colour Chart, 1995 Edition, except where general terms of ordinary dictionary significance are used.

Botanical classification: *Euphorbia pulcherrima* Willd. cultivar Eckakeem.

Parentage:

*Female parent.*—*Euphorbia pulcherrima* Willd. cultivar Gutbier Marlene, disclosed in U.S. Plant Pat. No. 8,735.

*Male parent.*—*Euphorbia pulcherrima* Willd. cultivar 792, not patented.

Propagation:

*Type cutting.*—Terminal cuttings.

*Time to initiate roots.*—About 10 days at 20 to 22° C.

*Time to develop roots.*—About 28 days at 24° C.

*Root description.*—Thick, fibrous and freely-branching.

Plant description:

*Plant form.*—Inverted triangle; top of plant mounded.

*Growth habit.*—Upright and uniform plant habit. Moderately vigorous to vigorous.

*Plant height.*—About 28 cm.

*Plant diameter or spread.*—About 44 cm.

*Lateral branch description.*—Quantity: About five lateral branches develop after pinching. Length: About 23.5 cm. Diameter: About 6 mm. Internode length: About 1.75 cm. Strength: Strong. Texture: Smooth; glabrous. Color: 146A.

*Foliage description.*—Arrangement: Alternate, single. Quantity of leaves per lateral branch: About ten. Length: About 12.5 cm. Width: About 9 cm. Shape: Elliptic. Apex: Acuminate. Base: Obtuse. Margin: Entire; with irregular lobing, about 3 shallow lobes. Venation pattern: Pinnate. Texture: Upper surface: Glabrous. Lower surface: Slightly pubescent. Surface: Slightly rugose. Aspect: Mostly flat. Orientation: Horizontal to slightly drooping. Color: Young foliage and fully expanded, upper surface: Darker than 147A. Young and fully expanded foliage, lower surface: 147A. Venation, upper and lower surfaces: 147C. Petiole: Length: About 6 cm. Diameter: About 3 mm. Texture, upper and lower surfaces: Smooth; glabrous. Color: 59A.

Inflorescence description:

*Inflorescence type and habit.*—Inflorescences are compound corymbs of cyathia with colored flower bracts subtending the cyathia. One inflorescence per lateral branch. Flowers are not fragrant. Flowers persistent.

*Natural flowering season.*—Autumn/winter in Northern Hemisphere. Flower initiation and development is induced under long nyctoperiod conditions. Early flowering, response time, about 9 weeks; natural season flower maturity date is early December for plants grown in Encinitas, Calif.

*Post-production longevity.*—Plants of the new Poinsettia maintain good substance and bract color for about four weeks under interior conditions.

*Inflorescence size.*—Diameter: About 30 cm. Height (depth): About 4 cm.

*Flower bracts.*—Quantity per inflorescence: About 22. Length, largest bracts: About 12.5 cm. Width, largest bracts: About 8 cm. Shape: Elliptic. Apex: Acute to slightly acuminate. Base: Cuneate to obtuse. Margin: Entire. Texture, upper and lower surfaces: Glabrous; velvety. Surface: Smooth. Aspect: Mostly flat. Orientation: Mostly horizontal. Venation pattern: Pinnate. Color: Developing or transitional bracts, upper surface: 46A. Developing or transitional bracts, lower surface: 53B. Fully developed bracts, upper surface: 53B; color does not fade with subsequent development. Fully developed bracts, lower surface: 53B to 53C. Venation, upper and lower surfaces: Similar to flower bract color. Bract petiole: Length: About 1.5 cm. Diameter: About 2 mm. Texture, upper and lower surfaces: Smooth; glabrous. Color: 53A.

*Cyathia.*—Quantity per corymb: About 15. Diameter of cyathia cluster: About 3.5 by 4 cm. Length: About 1.1 cm. Width: About 6 mm. Shape: Ovoid. Color: Immature: 144B. Mature: 144B to 144C. Peduncle: Length: About 2 mm. Diameter: About 2 mm. Strength: Strong. Aspect: Mostly upright. Texture: Smooth; glabrous. Color: 144C. Stamens: Quantity per cyathium: At least 15. Anther shape: Oval. Anther length: Less than 1 mm. Anther color: 59B. Amount of pollen: Moderate. Pollen color: 12A. Pistils: None observed. Nectaries: Quantity per cyathium: One or two. Size: About 4 mm by 6 mm. Color: 20A.

Disease/pest resistance: Resistance to pathogens and pests common to Poinsettias has not been observed on plants grown under commercial conditions.

It is claimed:

1. A new and distinct cultivar of Poinsettia plant named 'Eckakeem', as illustrated and described.

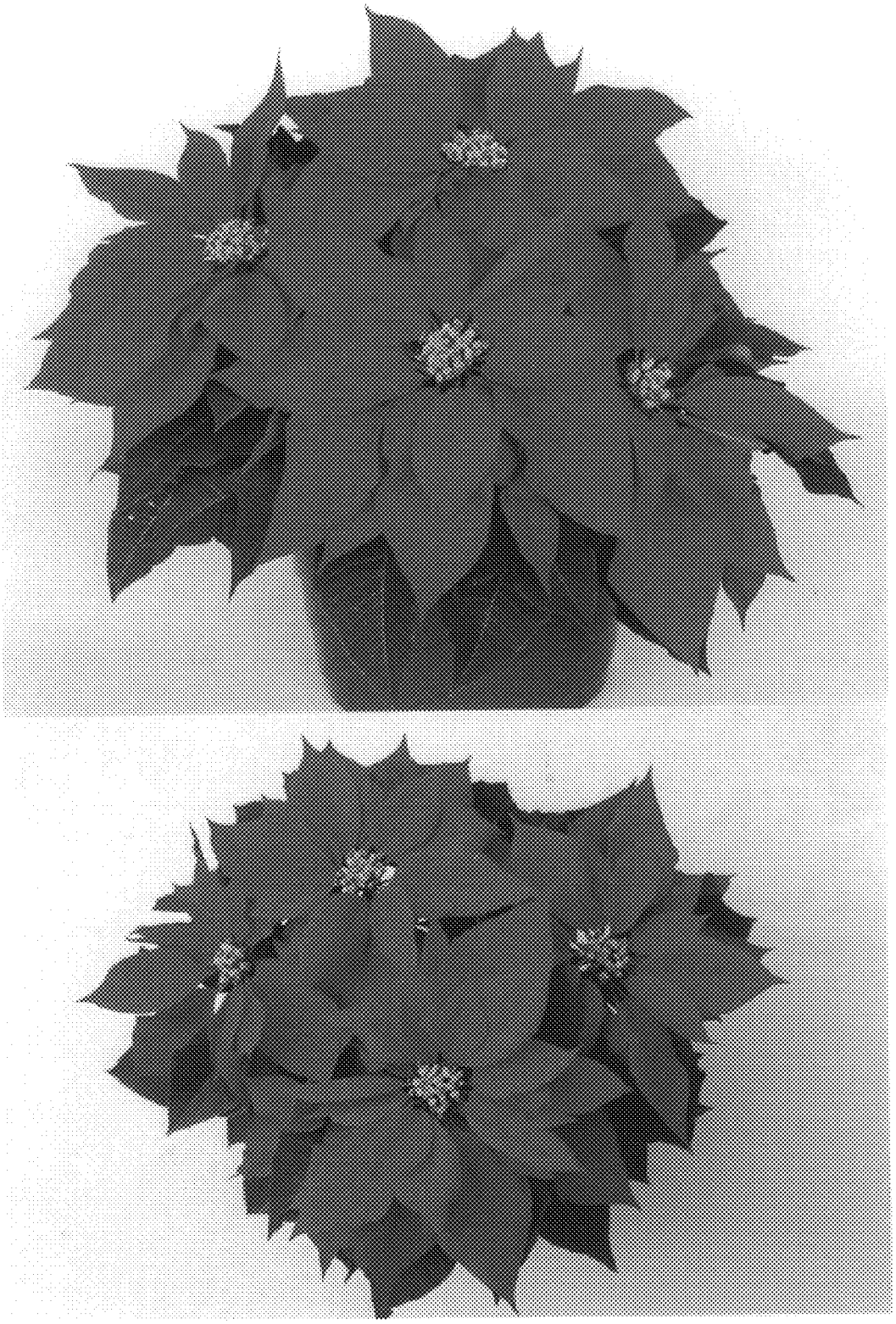

* * * * *